(12) United States Patent
Molnar-Kimber et al.

(10) Patent No.: US 7,897,733 B2
(45) Date of Patent: *Mar. 1, 2011

(54) RAPAMYCIN CONJUGATES AND ANTIBODIES

(75) Inventors: Katherine L. Molnar-Kimber, Worcester, PA (US); Craig E. Caufield, New York, NY (US); Timothy D. Ocain, Framingham, MA (US)

(73) Assignee: Pfizer, Inc., Madison, NJ (US)

( * ) Notice: Subject to any disclaimer, the term of this patent is extended or adjusted under 35 U.S.C. 154(b) by 355 days.

This patent is subject to a terminal disclaimer.

(21) Appl. No.: 11/272,070

(22) Filed: Nov. 14, 2005

(65) Prior Publication Data

US 2006/0121545 A1 Jun. 8, 2006

Related U.S. Application Data

(60) Continuation of application No. 10/124,386, filed on Apr. 18, 2002, now Pat. No. 7,279,562, which is a division of application No. 09/576,951, filed on May 24, 2000, now Pat. No. 7,279,561, which is a continuation-in-part of application No. 08/424,983, filed on Apr. 19, 1995, now abandoned, which is a continuation of application No. 08/224,205, filed on Apr. 14, 1994, now abandoned, which is a continuation-in-part of application No. 08/053,030, filed on Apr. 23, 1993, now abandoned.

(51) Int. Cl.
C07K 16/00 (2006.01)
C07K 1/04 (2006.01)
C12N 5/00 (2006.01)
C12P 21/08 (2006.01)

(52) U.S. Cl. ............... 530/388.9; 530/403; 435/345; 435/346; 435/70.21

(58) Field of Classification Search ........... 530/388.9, 530/402, 403, 807, 809; 436/548
See application file for complete search history.

(56) References Cited

U.S. PATENT DOCUMENTS

| | | | |
|---|---|---|---|
| 3,929,992 A | 12/1975 | Sehgal | |
| 3,993,749 A * | 11/1976 | Sehgal et al. | 424/122 |
| 4,208,479 A * | 6/1980 | Zuk et al. | 435/7.9 |
| 4,316,885 A | 2/1982 | Rakhit | |
| 4,401,653 A | 8/1983 | Eng | |
| 4,650,803 A | 3/1987 | Stella | |
| 4,885,171 A | 12/1989 | Surendra | |
| 5,023,264 A | 6/1991 | Caufield et al. | |
| 5,078,999 A | 1/1992 | Warner | |
| 5,080,899 A | 1/1992 | Sturm | |
| 5,089,390 A | 2/1992 | Davalian | |
| 5,091,389 A | 2/1992 | Ondeyka | |
| 5,100,883 A | 3/1992 | Schiehser | |
| 5,100,899 A | 3/1992 | Calne | |
| 5,102,876 A | 4/1992 | Caufield | |
| 5,118,677 A | 6/1992 | Caufield | |
| 5,118,678 A | 6/1992 | Kao | |
| 5,120,842 A | 6/1992 | Failli | |
| 5,122,511 A | 6/1992 | Patchett | |
| 5,130,307 A | 7/1992 | Failli | |
| 5,138,051 A | 8/1992 | Hughes | |
| 5,151,413 A | 9/1992 | Caufield | |
| 5,164,495 A | 11/1992 | Lunetta | |
| 5,169,773 A | 12/1992 | Rosenthaler | |
| 5,169,851 A | 12/1992 | Hughes | |
| 5,177,203 A | 1/1993 | Failli | |
| 5,194,447 A | 3/1993 | Kao | |
| 5,233,036 A | 8/1993 | Hughes | |
| 5,252,579 A | 10/1993 | Skotnicki | |
| 5,504,091 A | 4/1996 | Molnar-Kimber | |
| 5,532,137 A | 7/1996 | Niwa | |
| 5,665,772 A | 9/1997 | Cottens | |
| 5,912,253 A | 6/1999 | Cottens | |
| 5,985,890 A | 11/1999 | Cottens | |
| 6,187,547 B1 | 2/2001 | Legay | |
| 6,328,970 B1 | 12/2001 | Molnar-Kimber et al. | |
| 6,541,612 B2 * | 4/2003 | Molnar-Kimber et al. | 530/388.9 |
| 6,635,745 B2 | 10/2003 | Sedrani et al. | |
| 7,279,561 B1 * | 10/2007 | Molnar-Kimber et al. | 530/388.9 |
| 2002/0002273 A1 | 1/2002 | Sedrani et al. | |
| 2002/0022717 A1 | 2/2002 | Sedrani et al. | |

FOREIGN PATENT DOCUMENTS

| | | |
|---|---|---|
| EP | 0 201751 | 11/1986 |
| EP | 283801 | 3/1988 |
| EP | 473961 | 8/1991 |
| EP | 487289 | 11/1991 |
| EP | 467606 | 1/1992 |
| EP | 506032 | 3/1992 |
| EP | 507555 | 3/1992 |
| EP | 525960 | 6/1992 |
| EP | 693132 B1 | 1/1996 |
| JP | 63-219394 | 9/1988 |
| WO | WO 90/08957 | 8/1990 |
| WO | WO 90/06763 | 9/1990 |
| WO | WO 92/05179 | 4/1992 |
| WO | WO 92/22332 | 12/1992 |

(Continued)

OTHER PUBLICATIONS

Nolli et al. Antibodies against the antibiotics: an overview. Ann Ist Super Sanita 1991, vol. 27, Issue 1, pp. 149-154.*
Hultsch et al, *Proceedings of the National Academy of Sciences of USA*, 88:6229-6233 (1991).
Chen et al, *Journal of the American Chemical Society*, 116:2683-2684 (1994).
Sevier et al, *Clin. Chem.*, 27(11):1797-1806 (1981).
Yelton et al, *American Scientist*, 68:510-516 (1980).
Campbell et al, *Monoclonal Antibody and Immunosensor Technology*, Elsevier, Chapter 1 (1991).
Linskins et al, *Immunology in Plant Sciences*, pp. 86-141 (1986).

(Continued)

*Primary Examiner* — Shafiqul Haq
(74) *Attorney, Agent, or Firm* — A. David Joran

(57) ABSTRACT

Provided are rapamycin conjugates which are useful as immunogenic molecules for the generation of antibodies specific for rapamycin, for measuring levels of rapamycin or derivatives thereof; for isolating rapamycin binding proteins; and detecting antibodies specific for rapamycin or derivatives thereof. This invention also provides a rapamycin specific monoclonal antibody.

7 Claims, No Drawings

FOREIGN PATENT DOCUMENTS

| | | |
|---|---|---|
| WO | WO 93 19752 | 10/1993 |
| WO | WO 93 25533 | 12/1993 |
| WO | WO 94/24304 | 10/1994 |

OTHER PUBLICATIONS

Holt et al, *Chemical Abstracts*, vol. 120, No. 25 (1994).
Venzina et al, *J. Antibiot.*, 28:721 (1975).
Sehgal, *J. Antibiot.*, 28:727 (1975).
Baker, *Antibiot.*, 31:539 (1978).
Martel, *Can. J. Physiol. Pharmacol.*, 55:48 (1997).
Staruch, *FASEB*, 3:3411 (1989).
Dumont, *FASEB*, 3:5256 (1989).
Caine, *Lancet*, p. 1183 (1978).
Morris, *Med. Sci. Res.*, 17:877 (1989).
Baeder, *Fifth Int. Conf. Inflamm. Res. Assoc.*, Abstract, p. 121 (1990).
Gregory, *J. Heart Lung Transplant.*, 11(pt 2):197 (1992).
Meiser, *J. Heart Lung Transplant.*, 9:55 (1992).
Stepkowski, *Transplantation Proceedings*, 21(1):507-508 (1991).
Tamura, *Transplantation Proceedings*, 19(6):23-29 (1987).
Cadoff, *Transplantation Proceedings*, 22(1):50-51 (1990).
Propper, et al, FK506-Its Influence on Anti-Class 1 MHC Alloantibody Responses to Blood Transfusions, Transplantation, Aug. 1990, pp. 267-271, vol. 50, No. 2.
Tsuji, et al, Selective Immunosuppression of Prodigiosin 25-C and FK506 in the Murine Immune System, Oct. 1990, pp. 1293-1301, vol. 43, No. 10.
Van Duyne, et al, Atomic Structure of the Rapamycin Human Immunophilin FKBP-12 Complex, 1991, pp. 7433-7434, vol. 113.
Woo, et al, Spleen lymphocyte populations and expression of activation markers in rats treated with the potent new immunosuppressive agent FK-506, 1988, pp. 153-155, vol. 65.
English-language translation of Jun. 10, 2003 Official Action in Japanese Patent Application No. 524408/94.
English-language translation of May 11, 2004 Official Action in Japanese Patent Application No. 524408/94.
English-language translation of Sep. 29, 2009 Official Action on Appeal in Japanese Patent Application No. 524408/94 (Appeal No. 2006-5134).
English-language translation of Sep. 28, 2004 Official Action in Japanese Patent Application No. 2003-412071.
English-language translation of Dec. 13, 2005 Official Action in Japanese Patent Application No. 2003-412071.
English-language translation of Sep. 29, 2009 Official Action on Appeal in Japanese Patent Application No. 2003-412071 (Appeal No. 2006-4633).
English-language translation of Abstract of JP-63-219394 (Cite No. 3 herein).

* cited by examiner

RAPAMYCIN CONJUGATES AND ANTIBODIES

CROSS-REFERENCE TO RELATED APPLICATIONS

This application is a Continuation of U.S. application Ser. No. 10/124,386, filed Apr. 18, 2002 now U.S. Pat. No. 7,279,562; which is a Divisional Application of U.S. application Ser. No. 09/576,951, filed May 24, 2000 now U.S. Pat. No. 7,279,561; which is a Continuation-In-Part of U.S. application Ser. No. 08/424,983, filed Apr. 19, 1995 (now abandoned); which is a Continuation of U.S. application Ser. No. 08/224,205, filed Apr. 14, 1994 (now abandoned); which is a Continuation-In-Part of U.S. application Ser. No. 08/053,030, filed Apr. 23, 1993 (now abandoned). The entire disclosures of each of the prior applications, U.S. application Ser. Nos. 10/124,386, 09/576,951, 08/424,983, 08/224,205 and 08/053,030, are hereby incorporated by reference.

BACKGROUND OF THE INVENTION

This invention relates to derivatives of rapamycin which are useful as immunogenic molecules for the generation of antibodies specific for rapamycin, for measuring levels of rapamycin or derivatives thereof; for isolating rapamycin binding proteins; and detecting antibodies specific for rapamycin or derivatives thereof.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (198.9); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], adult T-cell leukemia/lymphoma [European Patent Application 525,960 A1], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,100,883 discloses fluorinated esters of rapamycin. U.S. Pat. No. 5,118,677 discloses amide esters of rapamycin. U.S. Pat. No. 5,118,678 discloses carbamates of rapamycin. U.S. Pat. No. 5,130,307 discloses aminoesters of rapamycin. U.S. Pat. No. 5,177,203 discloses sulfonates and sulfamates of rapamycin. U.S. Pat. No. 5,194,447 discloses sulfonylcarbamates of rapamycin. PCT Publication WO 92/05179 discloses carboxylic acid esters of rapamycin.

Yatscoff has reported that rapamycin levels can be quantitated using HPLC method with a sensitivity of 1 ng/ml [Ther. Drug Monitoring 14: 138 (1992)]. This method is time consuming and each sample must be assayed individually.

Immunoassays have been developed for numerous proteins as well as various drugs including cyclosporin A [Morris, R. G., Ther. Drug Monitoring 14: 226-(1992)], and FK506 [Tamura, Transplant Proc. 19: 23 (1987); Cadoff, Transplant Proc. 22: 50 (1990)]. Numerous types of immunoassays, that have been developed to measure proteins or compounds, have been based on competitive inhibition, dual antibodies, receptor-antibody interactions, antigen capture, dipstick, antibody or receptor trapping, or on affinity chromatography. Affinity columns with rapamycin have been reported in which a rapamycin analog was covalently attached to a matrix [Fretz J. Am. Chem. Soc. 113: 1409 (1991)]. These columns have been used to isolate rapamycin binding proteins.

DESCRIPTION OF THE INVENTION

This invention provides a rapamycin conjugate of formula I, having the structure

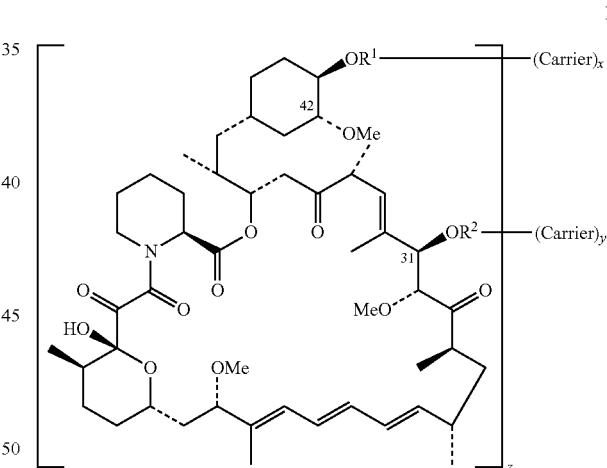

wherein
$R^1$ and $R^2$ are each, independently, hydrogen or —($R^3$-L-$R^4$)$_a$—;
L is a linking group;
$R^3$ is selected from the group consisting of carbonyl, —S(O)—, —S(O)$_2$—, —P(O)$_2$—, —P(O)(CH$_3$)—, —C(S)—, and —CH$_2$C(O)—;
$R^4$ is a selected from the group consisting of carbonyl, —NH—, —S—, —CH$_2$—, and —O—:
a=1-5;
x=0-1;
y=0-1;
z is from about 1 to about 120;
and Carrier is immunogenic carrier material, detector carrier material, or a solid matrix, or a salt thereof with the proviso that $R^1$ and $R^2$ are both not hydrogen; and further provided that when a is greater than 1, each L group can be the same or different; and still further provided that x is 0 if $R^1$ is hydrogen and y is 0 if $R^2$ is hydrogen, and if x and y are both 1, the Carrier moiety is the same in both cases.

The linking group, L, is any moiety that contains the group $R^3$ on one end and $R^4$ on other end, therefore enabling the linking group to be connected to the 42- and/or 31-hydroxyl groups of rapamycin on one end and connected to another linking group or the immunogenic carrier material, detector material, or matrix on the other end. When a is greater than 1, each L group can be the same or different. In such cases, the first L group is designated as $L^1$, the second L group designated as $L^2$ and so on. The rapamycin conjugates of the present invention may be prepared in such ways as to encompass a wide range of linking groups (L) and terminal functional groups $R^4$. For example, L may be linear or branched alkylenes comprising from 1 to as many as 15, more usually 10 or less, and normally less than 6 carbon atoms (i.e., methylene, ethylene, n-propylene, iso-propylene, n-butylene, and so forth). In addition, such alkylenes can contain other substituent groups such as cyano, amino (including substituted amino), acylamino, halogen, thiol, hydroxyl, carbonyl groups, carboxyl (including substituted carboxyls such as esters, amides, and substituted amides). The linking group L can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, amino, thio ether, amidino, sulfone, or sulfoxide. Also, such linkages can include unsaturated groupings such as olefinic or acetylenic bonds, disulfide, imino, or oximino groups. Preferably L will be a chain, usually aliphatic comprising between 1 and about 20 atoms, more usually between 1 and 10, excluding hydrogen, of which between 0 and 5 are heteroatoms preferably selected from nitrogen, oxygen, and sulfur. Therefore, the choice of linking group L is not critical to the present invention and may be selected by one of ordinary skill taking normal precautions to assure that stable compounds are produced.

A preferred embodiment of this invention provides a conjugate of formula II, having the structure

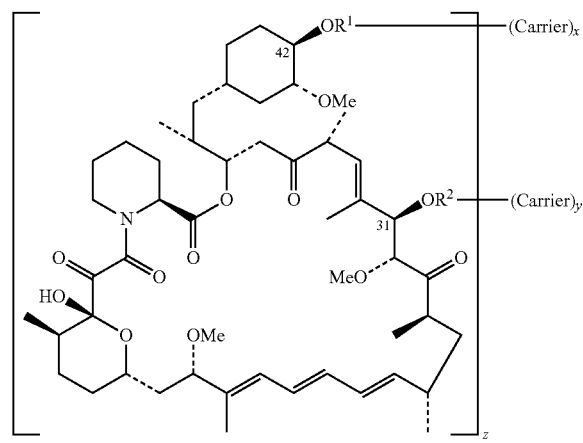

II $R^1$ and $R^2$ are each, independently, hydrogen or —$R^3$-L-$R^4$—;

L is -A(CR$^5$R$^6$)$_b$[B—(CR$^7$R$^8$)$_d$]$_e$—

A is —CH$_2$— or —NR$^9$—;

B is —O—, —NR$^9$—, —S—, —S(O)—, or —S(O)$_2$—;

$R^3$ is selected from the group consisting of carbonyl, —S(O)—, —S(O)$_2$—, —P(O)$_2$—, —P(O)(CH$_3$)—, —C(S)—, and —CH$_2$C(O)—;

$R^4$ is selected from the group consisting of carbonyl, —NH—, —S—, —CH$_2$—, and —O—;

$R^5$, $R^6$, $R^7$, and $R^8$ are each, independently, hydrogen, alkyl of 1-6 carbon atoms, alkenyl of 2-7 carbon atoms, alkynyl of 2-7 carbon atoms, halo, hydroxy, trifluoromethyl, arylalkyl of 7-10 carbon atoms, aminoalkyl of 1-6 carbon atoms, hydroxyalkyl of 1-4 carbon atoms, alkoxy of 1-6 carbon atoms, carbalkoxy of 2-7 carbon atoms, cyano, amino, —CO$_2$H, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

$R^9$ is hydrogen, alkyl of 1-6 carbon atoms, or aralkyl of 7-10 carbon atoms;

b=0-10;

d=0-10;

e=0-2;

x=0-1;

y=0-1;

z is from about 1 to about 120;

and Carrier is immunogenic carrier material, detector carrier material, or a solid matrix, or a salt thereof with the proviso that $R^1$ and $R^2$ are both not hydrogen; and further provided that when b is greater than 1, each of the CR$^5$R$^6$ groups can be the same or different, and when d is greater than 1, each of the CR$^7$R$^8$ groups can be the same or different; and still further provided that x is 0 if $R^1$ is hydrogen and y is 0 if $R^2$ is hydrogen, and if x and y are both 1, the Carrier moiety is the same in both cases.

A second preferred embodiment of this invention provides a conjugate of formula III, having the structure

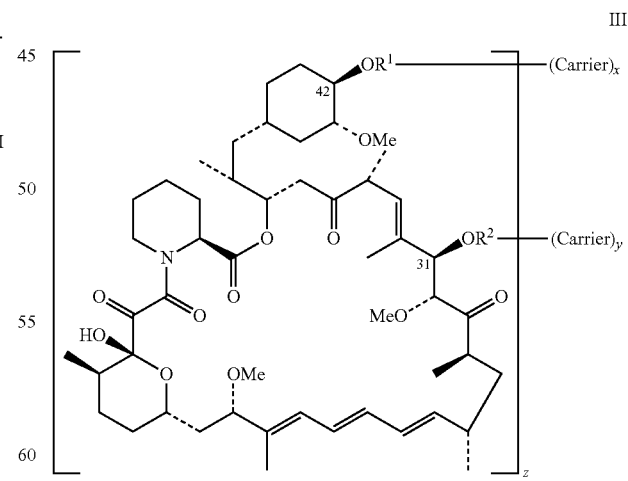

III $R^1$ and $R^2$ are each, independently, hydrogen or —($R^3$-$L^1$-$R^4$)$_f$—($R^{10}$-$L^2$-$R^{11}$)$_g$-Carrier;

$L^1$ is —(CH$_2$)$_h$—CHR$^{12}$—(CH$_2$)$_j$—;

$L^2$ is —(CH$_2$)$_k$-D-(CH$_2$)$_m$-E-;

D is —CH$_2$—, —S—S—, or

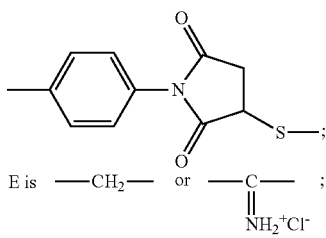

E is —CH$_2$— or —C—
                    ‖
                    NH$_2^+$Cl$^-$ ;

R$^3$ and R$^{10}$ are each, independently, selected from the group consisting of carbonyl, —S(O)—, —S(O)$_2$, —P(O)$_2$—, —P(O)(CH$_3$)—, —C(S)—, and —CH$_2$C(O)—;

R$^4$ and R$^{11}$ are each, independently, selected from the group consisting of carbonyl, —NH—, —S—, —CH$_2$—, and —O—;

R$^{12}$ is hydrogen, alkyl of 1-6 carbon atoms, arylalkyl of 7-10 carbon atoms, alkenyl of 2-7 carbon atoms, alkynyl of 2-7 carbon atoms, —(CH$_2$)$_n$CO$_2$R$^{13}$, —(CH$_2$)$_n$NR$^{14}$R$^5$, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 14 carbon atoms, alkylthioalkyl of 2-6 carbon atoms, indolylmethyl, hydroxyphenylmethyl, imidazoylmethyl, halo, trifluoromethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

R$^{14}$, and R$^{15}$ are each, independently, hydrogen, alkyl of 1-6 carbon atoms, or arylalkyl of 7-10 carbon atoms;

R$^{13}$ is hydrogen, alkyl of 1-6 carbon atoms, arylalkyl of 7-10 carbon atoms, alkenyl of 2-7 carbon atoms, alkynyl of 2-7 carbon atoms, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

f=0-3;
g=0-1;
j=0-10;
k=0-10;
m=0-10;
n=0-6;
p=0-6;
x=0-1;
y=0-1;
z is from about 1 to about 120;

and Carrier is immunogenic carrier material, detector carrier material, or a solid matrix, or a salt thereof with the proviso that R$^1$ and R$^2$ are both not hydrogen; and further provided that f and g are both not 0 and when f is greater than 1, each of the —(R$^3$-L$^1$-R$^4$)— moieties can be the same or different; and still further provided that x is 0 if R$^1$ is hydrogen and y is 0 if R$^2$ is hydrogen, and if x and y are both 1, the Carrier moiety is the same in both cases.

This invention also provides a conjugate of formula IV, having the structure

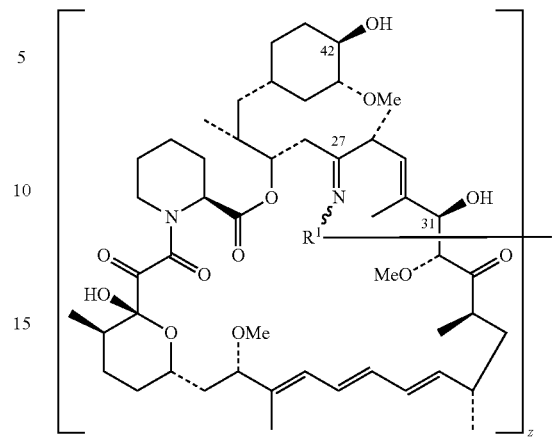

wherein
R$^1$ is —OCH$_2$(CH$_2$)$_q$R$^4$—;
R$^4$ is selected from the group consisting of carbonyl, —NH—, —S—, —CH$_2$—, and —O—;
q=0-6;
z is from about 1 to about 120;
and Carrier is immunogenic carrier material, detector carrier material, or a solid matrix; or a salt thereof.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000 and more usually greater than 40,000. Generally, proteins taken from one animal species will be immunogenic when introduced into the blood stream of another species. Particularly useful proteins are those such as albumins, globulins, enzymes, hemocyanins, glutelins or proteins having significant non-proteinaceous constituents, e.g., glycoproteins, and the like. Further reference for the state-of-the-art concerning conventional immunogenic carrier materials and techniques for coupling haptens thereto may be had to the following: Parker, Radioimmunoassay of Biologically Active Compounds, Prentice-Hall (Englewood Cliffs, N.J., USA, 1976), Butler, J. Immunol. Meth. 7:1-24 (1975) and Pharmacol. Rev. 29(2):103-163 (1978); Weinryb and Shroff, Drug Metab. Rev. 10:P271-283 (1975); Broughton and Strong, Clin. Chem. 22:726-732 (1976); and Playfair et al., Br. Med. Bull. 30:24-31 (1974). Preferred immunogenic carrier materials for use in the present invention are ovalbumin and keyhole limpet hemocyanin. Particularly preferred for use in the present invention is ovalbumin. The detector carrier material can be a rapamycin-linking moiety conjugated to an enzyme such as horseradish peroxidase, alkaline phosphatase, luciferase, a fluorescent moiety such as fluorescein, Texas Red, or rhodamine, a chemiluminescent moiety, and the like. The solid matrix carrier material can be resin beads, an ELISA plate, glass beads as commonly used in a radioimmunoassay, plastic beads, solid matrix material typically used in a dipstick-type assay. When rapamycin is conjugated to a solid matrix, the resulting conjugate can be used in a dipstick assay, as described in this disclosure, for the affinity purification of antibodies, or for isolating rapamycin binding proteins.

It should be noted that as used in the formulae above describing the specific rapamycin conjugates, z represents the number of rapamycin conjugated to the carrier material. The value z is sometimes referred to as the epitopic density of the immunogen, detector, or solid matrix and in the usual situation will be on the average from about 1 to about 120 and more typically from 1 to 50. The densities, however, may vary greatly depending on the particular carrier material used.

When any of the compounds of this invention contain an aryl or arylalkyl moiety, it is preferred that the aryl portion is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl group that may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$. It is more preferred that the aryl moiety is a phenyl group that is optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$.

The salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention can be prepared by reacting the 42- and/or 31-hydroxyl groups of rapamycin with a suitable electrophilic reagent that will serve as the linker moiety. The following patents exemplify the preparation of the 42- and/or 31-derivatives of rapamycin that can be used as linking groups for the preparation of the compounds of this invention. The preparation of fluorinated esters of rapamycin is described in U.S. Pat. No. 5,100,883. The preparation of amide esters is disclosed in U.S. Pat. No. 5,118,677. The preparation of carbamates of rapamycin is disclosed in U.S. Pat. No. 5,118,678. The preparation of aminoesters of rapamycin is described in U.S. Pat. No. 5,130,307. The preparation of sulfonates and sulfamates of rapamycin are described in U.S. Pat. No. 5,177,203. The preparation of sulfonylcarbamates of rapamycin are described in U.S. Pat. No. 5,194,447. The disclosures of the above cited U.S. Patents are hereby incorporated by reference. From these patents, it can be seen that reactive electrophiles such as isocyanates, used in the preparation of carbamates, or sulfonyl chlorides, used in the preparation of sulfonates, can be reacted with the hydroxyl groups of rapamycin without the need for an activating agent. For the esterification of the rapamycin hydroxyl groups with a carboxylic acid, activation is usually required through the use of a coupling reagent such as DCC, or a water soluble analog thereof, such as dimethylaminopropyl)-3-ethyl carbodiimide (DAEC). Representative examples of the preparation of rapamycin-linking group moieties are provided as examples below. The preparation of ether derivatives of rapamycin can be accomplished using the methodology disclosed in Example 18.

For the compounds of this invention in which the linker group is attached to the 42- or the 31,42-hydroxyls, the electrophile (or activated electrophile) is reacted with rapamycin to typically provide a mixture of the 42- and 31,42-derivatized rapamycin that can be separated by chromatography. For the compounds of this invention in which the linker group is attached to the 31-hydroxyl of rapamycin, the 42-hydroxyl group must be protected with a suitable protecting group, such as with a tert-butyldimethyl silyl group. The 31-hydroxyl can then be reacted with a suitable electrophile to provide the derivatized rapamycin, followed by deprotection of the 42-hydroxyl group. The preparation of 42-O-silyl ethers of rapamycin and subsequent deprotection is described in U.S. Pat. No. 5,120,842, which is hereby incorporated by reference. Preparation of compounds containing different linkers at the 31- and 42-positions can be accomplished by first preparing the 42-derivatized compound and then using a different linker to derivatize the 31-position. The preparation of the 27-oxime linking groups can be accomplished using the methodology disclosed in U.S. Pat. No. 5,023,264, which is hereby incorporated by reference; and as described in Example 21.

The linker group attached to rapamycin can be coupled to a second linker group using standard methodology described in the peptide literature; typically by activating the electrophilic moiety, with DCC type coupling reagent, or with N-hydroxysuccininide, or as an activated ester or anhydride. The activated electrophilic end of one linking moiety can then be reacted with the nucleophilic end of the other linker moiety.

The coupling of the rapamycin linking group moiety to the immunogenic carrier can be accomplished under standard literature conditions. In general, for reaction with a nucleophilic group on the immunogenic carrier material, an electrophilic moiety, such as a carboxylic acid, on the linking group is activated with a suitable activating agent such as N-hydroxysuccinimide, and then reacted with the nucleophilic moiety on the immunogenic carrier material. Examples 2 and 3 specifically exemplify this technique. Similar methodology is employed for the coupling of a nucleophilic moiety on the linking group to an electrophilic moiety on the immunogenic carrier material. In such cases, the electrophilic moiety on the immunogenic carrier material is activated as described above, and then reacted with the nucleophilic end of the linking group.

The reagents used to prepare the compounds of the invention are commercially available or can be prepared by methods that are disclosed in the literature.

This invention also covers analogous conjugates of other rapamycins such as, but not limited to, 29-demethoxyrapamycin, [U.S. Pat. No. 4,375,464,32-demethoxyrapamycin under C.A. nomenclature]; rapamycin derivatives in which the double bonds in the 1-, 3-, and/or 5-positions have been reduced [U.S. Pat. No. 5,023,262]; 42-oxorapamycin [U.S. Pat. No. 5,023,262]; 27-oximes of rapamycin [U.S. Pat. No. 5,023,264]; 27-hydrazones of rapamycin [U.S. Pat. No. 5,120,726]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxy- and 15,27-bishydroxy-rapamycin [U.S. Pat. No. 5,102,876]. The disclosures in the above cited U.S. Patents are hereby incorporated by reference. Also covered are conjugates of the rapamycin 1,3-Diels Alder adduct with diethyl azidodicarboxylate and rapamycin 1,3-Diels Alder adduct with phenyltriazoline dione. The preparation of these compounds is described in Examples 14 and 15.

The compounds of this invention are rapamycin immunogen, detector, and matrix bound conjugates that are useful for the generation and detection of antibodies specific for rapamycin and derivatives thereof, for measuring levels of rapamycin or a derivative thereof in biological or laboratory fluids, and for isolating rapamycin binding proteins. Rapamycin derivatives as defined here are compounds containing a rapamycin nucleus in which one or more of the hydroxyl groups has been esterified into a carboxylic ester, a carbamate, a sulfonate ester, an amide, or the like, or one or more of the ketones has been reduced to a hydroxyl group, or one or more of the double bonds has been reduced, or one ketones has been converted to an oxime or a hydrazone. Other rapamycin derivatives for which the compounds of this invention can be used for measuring levels of or generating antibodies to will be apparent to one skilled in the art based on this disclosure.

Antibodies specific for rapamycin using the rapamycin immunogen conjugates of this invention may be generated by standard techniques that are known in the art. Typically, a host animal is inoculated at one or more sites with the immunogen conjugate, either alone or in combination with an adjuvant. The typical host mammals include, but are not limited to, mice, goats, rabbits, guinea pigs, sheep, or horses. Subsequent injections can be made until a sufficient titer of antibodies are produced. The antibodies generated from the rapamycin immunogen conjugates of this invention can be used in numerous immunoassays, for determining rapamycin levels, in ELISAs, radioimmunoassays, in chemiluminesence immunoassays, and in fluorescent immunoassays. Although many variations of the immunoassay can be used (antigen capture, antibody capture, competitive inhibition, or two antibody immunoassay), a basic competitive inhibition immunoassay can be performed as follows: Antibody specific for the ligand is usually bound to a matrix. A solution is applied to decrease nonspecific binding of the ligand to the matrix. After rinsing the excess away, the antibody coupled matrix may be treated in some cases so it can be stored. In a competitive inhibition assay, the ligand standard curve is made and added with the rapamycin detector conjugate to compete for binding to the rapamycin-specific antibody. If necessary, the excess is removed. The detector molecule is detected by the standard methods used by one skilled in the art. Different formats can be used, which include but are not limited to, dipstick assays, FPIA, EMIT, ELISA, VISTA, RIA, and MEIA. Detector conjugates of the present invention can be prepared to use in the above assays. For example, the detector conjugates can be Carrier material with labeled fluorescent, chemiluminescent, or enzymatic moieties.

This invention also provides for the use of the rapamycin immunogen conjugates or rapamycin specific antibodies in a test kit that can be commercially marketed. The test kit may be used for measuring levels of rapamycin in biological or laboratory fluids. Test kit components may include rapamycin antibodies, antisera, or rapamycin carrier conjugates. The conjugates or antibodies may be bound to a solid matrix, and rapamycin derivatives or antibodies may be radiolabeled if the assay so requires. Standard concentrations of rapamycin can be included so that a standard concentration curve can be generated. Suitable containers, microtiter plates, solid supports, test tubes, trays, can also be included in any such kit. Many variations of reagents can be included in the kit depending on the type of assay used.

The following is illustrative of the use of a rapamycin immunogen conjugate of this invention to generate rapamycin specific antibodies and detect them using an ELISA format immunoassay. Five mice were immunized with 50 µg rapamycin 31,42-diester with glutaric acid conjugate with keyhole limpet hemocyanin in Complete Freund's Adjuvant intrasplenically and after about one month were boosted with 50 µg of rapamycin 31,42-diester with glutaric acid conjugate with keyhole limpet hemocyanin in incomplete Freund's Adjuvant into the footpads. Microtiter plates (IMMUNO-LON I) were coated overnight with 100 µl of goat anti-mouse antibody (10 µg/ml in 10 mM potassium phosphate buffer, pH 7.2) at 4° C. The plates were flicked and blocked with 100 µl of 1% bovine sera albumin in phosphate buffered saline overnight at 4° C. After flicking and washing the plates thrice with 10 mM phosphate buffer, pH 7.05, 30 mM NaCl, 0.02% TRITON X-100 (polyethylene glycol tert-octylphenyl ether), and 0.004% thimerosal wash buffer, 100 µl of each mouse sera-diluted with phosphate buffer solution was added to a well and incubated at room temperature for overnight. After flicking and washing the plates thrice with wash buffer, rapamycin 31,42-diester with glutaric acid conjugate with horseradish peroxidase (compound of Example 10 (100 µl, 0.5 ng/ml)) was added and incubated for 1 hour at room temperature in the dark. After flicking and washing the plates thrice with wash buffer, tetramethyl benzidine (TMB) substrate with $H_2O_2$ was added and the plates were incubated covered for 30 min. at room temperature in the dark. The optical density was read on a spectrophotometer at 450 nm. As shown in Table I, five mice had antibodies reactive for rapamycin 31,42-diester with glutaric acid conjugate with horseradish peroxidase (compound of Example 10).

TABLE I

| MOUSE # | DILUTION[a] | O.D. |
|---|---|---|
| 6902 | 1/300 | 0.199 |
| 6903 | 1/100 | 0.231 |
| 6904 | 11500 | 0.412 |
| 6905 | 11100 | 0.121 |
| 6906 | 1/300 | 0.321 |
| background | — | 0.076 |

[a]Dilution of mouse sera in PBS

The results in Table 1 show that mouse 6904 produced the most antibodies to the compound of Example 10. Hybridomas were generated using standard methodology. Following a splenectomy of a mouse immunized and boosted 3 times with the compound of Example 4, spleen cells were fused to SP20 cells to produce hybridomas. The hybridomas were evaluated for the production of rapamycin specific antibodies using an ELISA assay as briefly described below.

Microtiter plates (IMMUNOLON I) were coated overnight with 100 µl of goat anti-mouse antibody (10 µg/ml in 10 mM potassium phosphate buffer, pH 7.2) at 4° C. The plates were flicked and blocked with 100 µl of 1% bovine sera albumin in phosphate buffered saline (PBS) overnight at 4° C. After flicking and washing the plates thrice with 0.2×PBS containing 0.02% TRITON X-100 and 0.004% thimerosal, 100 µl of each hybridoma supernatant was added to a well and incubated at room temperature for overnight. After flicking and washing the plates thrice with 0.2×PBS containing 0.02% TRITON X-100 and 0.004% thimerosal, the compound of Example 22 (100 µl, 0.17 µM) was added and incubated for 1 hour at 4° C. After flicking and washing the plates thrice with 0.2×PBS containing 0.02% TRITON X-100 and 0.004% thimerosal, strepavidin or avidin conjugated to horseradish peroxidase (100 µl, 0.2 µg/ml) was added and incubated at room temperature for 1 hour in the dark. After flicking and washing the plates thrice with 0.2×PBS containing 0.02% TRITON X-100 and 0.004% thimerosal, TMB substrate and $H_2O_2$ was added and the plates were incubated covered for 30 min. at room temperature in the dark. The optical density was read on a spectrophotometer at 450 nm. An optical density reading of 0.25-3 indicates specific antibody binding. The results in Table 2 show that the hybridoma from well P4G1 is positive for binding to the compound of Example 22, and is therefore specific for rapamycin.

TABLE 2

Screening for Rapamycin Specific Monoclonal Antibodies

| WELL | OPTICAL DENSITY |
|---|---|
| P3H4 | 0.120 |
| P3H5 | 0.105 |
| P4G1 | 1.940 |

The hybridoma cell line in P4G1 was cloned by limiting dilution and is designated as hybridoma cell line, RAP-42-OVAF$_2$#1hc. The rapamycin-specific antibody, designated as RAP-42-OVAF$_2$#1MoAb, was isolated and purified using conventional methodology. Hybridoma RAP-42-OVAF$_2$#1hc was deposited under the terms of the Budapest Treaty at the American Type Culture Collection, 10801 University Boulevard, Manassas, VIRGINIA 20110-2209, USA, on Mar. 10, 1994, and was granted accession number HB 11568.

The compounds of Examples 12 and 13 can be used in an assay for the detection of polyclonal antibodies and monoclonal antibodies specific for rapamycin as described below.

Microtiter plates (IMMUNOLON I) were coated overnight with 100 µl of goat anti-mouse antibody (10 µg/ml in 10 mM potassium phosphate buffer, pH 7.2) at 4° C. The plates were flicked and blocked with 100% of 1% bovine sera albumin in phosphate buffered saline overnight at 4° C. After flicking and washing the plates thrice with wash buffer, 100 µl of rabbit sera diluted 1:5 in phosphate buffered saline was added to a well and incubated at room temperature for overnight. After flicking and washing the plates thrice with wash buffer, rapamycin 42-ester with 3-[3-(4-imino-butylthio)succinimidyl] phenacylglycine conjugate with horseradish peroxidase (compound of Example 12) (100 µl, 0.5 ng/ml) or rapamycin 42 ester with (N-(3-carboxyphenyl)-3-thiosuccinimidyl)glycine conjugate with horseradish peroxidase (compound of Example 13) (100 µl, 0.5 ng/ml) was added and incubated for 1 hour at room temperature in the dark. After flicking and washing the plates thrice with wash buffer, TMB substrate with $H_2O_2$ was added and the plates were incubated covered for 30 min. at room temperature in the dark. The optical density was read on a spectrophotometer at 450 nm. The results are shown in Table III.

TABLE 3

Comparison of Anti-rapamycin Antibody Levels in Rabbits Immunized with the Compound of Example 3 vs. Naive Rabbits Using a Capture ELISA Assay

| | Prebleed | | ΔA450 (3rd Bleed-Prebleed) | |
|---|---|---|---|---|
| Rabbit No. | Example 10 | Example 10 | Example 12 | Example 13 |
| 81 | 0.119 | 0.713 | 0.217 | 0.114 |
| 89 | 0.136 | 0.037 | 0.026 | 0.020 |

The data in Table 3 show that the compounds of Examples 12 and 13 can be used to detect antibodies specific for rapamycin in an a mammal, as seen in rabbit number 81.

The following is an example of the measurement of rapamycin concentrations using a competitive inhibition assay for rapamycin with an ELISA format using an antibody specific for rapamycin. Microtiter plates (IMMUNOLON I) were coated overnight with 100 µl of goat anti-mouse antibody (10 µg/ml in 10 mM potassium phosphate buffer, pH 7.2) at 4° C. The plates were flicked and blocked with 100 µl of 1% bovine sera albumin in phosphate buffered saline overnight at 4° C. After flicking and washing the plates thrice with wash buffer, the rapamycin specific antibody described above (100 µl of 1 µg/ml) was added to each well and incubated at room temperature for 1-4 hour. After flicking and washing the plates thrice with wash buffer, rapamycin 31,42-bis(hemiglutarate) conjugate with horseradish peroxidase (100 µl, 0.5 ng/ml) was added and incubated for 1 hour at room temperature in the dark. After flicking and washing the plates thrice with wash buffer, TMB substrate was added and the plates were incubated covered for 5 min at room temperature in the dark. The optical density was read on a spectrophotometer at 450 nm. Results of the competition between rapamycin and rapamycin 31,42-diester with glutaric acid conjugate with horseradish peroxidase binding to mouse sera are shown in Table 4. From these results, a standard curve can be constructed and the concentration of rapamycin in a sample can be determined.

TABLE 4

| Free | OPTICAL DENSITY × 1000 | | | |
|---|---|---|---|---|
| RAPAMYCIN | 1 | 2 | Avg | % Inhibition |
| 10 µM | 158 | 158 | 158 | 74.1 |
| 5 | 182 | 194 | 188 | 69.2 |
| 0.5 | 304 | 322 | 313 | 48.6 |
| 0.05 | 494 | 501 | 498 | 18.4 |
| 0.005 | 528 | 546 | 537 | 11.9 |
| 0.0005 | 601 | 611 | 606 | 0.6 |
| 0 | 583 | 636 | 610 | — |

The compound of Example 11 (rapamycin 42-ester with N-[9H-fluoren-9-ylmethoxy)carbonyl]glycine) can be deprotected by the procedure used in Example 12 (to give rapamycin 42-ester with glycine) and conjugated to a solid matrix. It can bind rapamycin specific antibodies as used in some dipstick immunoassay methods or to isolate rapamycin binding proteins. The following example illustrates that 803 resonance units (RU) of the compound of Example 11 can be immobilized on a solid matrix using the BIAcore's standard protocol based on EDC and NHS used in a BIAcore. This matrix bound 1401 RU units of rapamycin specific antibody. The kinetics of association and dissociation were determined for each concentration of antibody tested (0.625, 1.25, 2.5, 5.0, 10.0 ug/ml). These data show that the compound of Example 11, even when bound to a matrix was accessible to binding by a rapamycin-specific antibody and the interaction could be characterized. Similar procedures can be used to bind a rapamycin-binding protein to deprotected rapamycin 42-ester with N-[9H-fluoren-9-ylmethoxy)carbonyl]glycine conjugated matrix. This matrix can also be used for the isolation of novel binding proteins, as practiced by one skilled in the art. Deprotected rapamycin 42-ester with N-[9H-fluoren-9-ylmethoxy)carbonyl]glycine can be used to isolate binding proteins of rapamycin-FKBP complex by one of the following methods. In one approach, tissue or cell lysates containing the appropriate protease inhibitors are incubated with FKBP which has been incubated with a deprotected-rapamycin 42-ester with N-[9H-fluoren-9-ylmethoxy)carbonyl]glycine conjugated matrix for a sufficient time to allow binding. Various buffers are used to rinse the proteins which are nonspecifically bound. Proteins are released by the addition of additional buffers which disrupt the bond between the rapamycin nucleus-FKBP and the binding proteins.

The following examples represent the preparation of representative compounds of this invention.

Example 1

Rapamycin 42-ester with Succinic Acid 1.1 g (11 mmol) of succinic anhydride and 400 mg of dimethylaminopyridine (DMAP) were added to a stirring solution of 5 g (5.5 mmol) of rapamycin and 880 μl of pyridine in 15 ml of methylene chloride. The reaction mixture was stirred for 2 days at room temperature, diluted with methylene chloride and washed with three 50 ml portions of 1N HCl. The organic layer was then dried over $Na_2SO_4$ and concentrated in vacuo affording crude product. Pure material was obtained by reverse phase HPLC with 53% acetonitrile/water as eluant affording 1 g (18%) of the title compound. Spectral data follows: $^1$H NMR ($CDCl_3$, 300 MHz) 4.650 (m, 1H, $H_2COC=O$), 4.168 (d, 1H, $H_2COH$), 2.795 (s, 4H, $OC=OCH_2CH_2C=O$).

Example 2

Rapamycin 42-ester with (N-hydroxysuccinimide(hemisuccinate))

21 mg (0.098 mmol) of DCC and 12 mg (0.098 mmol) of Nhydroxysuccinimide were added to a stirring solution of 100 mg of rapamycin 42-ester with succinic acid in 3 ml ethyl acetate. The reaction mixture was stirred overnight at room temperature, filtered, and concentrated in vacuo affording crude product. Pure material was obtained by reverse phase HPLC with 80% acetonitrile/water as eluant affording 75 mg (69%) of the title compound. Spectral data follows: $^1$H NMR ($CDCl_3$, 300 MHz) 4.650 (m, 1H, $H_2COC=O$), 4.168 (d, 1H, $H_2COH$), 2.951 (m, 2H, $OC=OCH_2$), 2.795 (m, 4H, $OC=OCH_2CH_2C=O$), 2.705 (m, 2H, $OC=OCH_2$); MS (neg.ion FAB) 1110 ($M^-$), 1056, 1012, 913, 148 (100).

Example 3

Rapamycin 42-ester with Succinic Acid Conjugate with Keyhole Limpet Hemocyanin 197 mg of keyhole limpet hemocyanin in 6 ml of 0.05 M phosphate buffer was added to a stirring solution of 37 mg of rapamycin 42-ester with (N-hydroxysuccinimide(hemisuccinate)) in 3 ml of 1,4 dioxane and the reaction was left stirring for 3 days at 4° C. The reaction mixture was then dialyzed for 24 hr at 4° C. in 1500 ml of 0.05 M phosphate buffer to give the title compound which could be used without further purification. The number of rapamycin 42-ester with succinic acid moieties per keyhole limpet hemocyanin was approximately 42:1.

Example 4

Rapamycin 42-ester with Succinic Acid Conjugate with Ovalbumin 197 mg of ovalbumin in 6 ml of 0.05 M phosphate buffer was added to a stirring solution of 37 mg of rapamycin 42-ester with (N-hydroxysuccinimide(hemisuccinate)) in 3 ml of 1,4 dioxane and the reaction was left stirring for 3 days at 4° C. The reaction mixture was then dialyzed for 24 hr at 4° C. in 1500 ml of 0.05 M phosphate buffer to give the title compound which could be used without further purification.

Example 5

Rapamycin 42-ester with Succinic Acid Conjugate with Horseradish Peroxidase 16 mg of horseradish peroxidase in a solution of 0.4 ml of 1,4 dioxane and 0.4 ml of 0.5% sodium bicarbonate was added to 1 mg of rapamycin 42-ester with (N-hydroxysuccinimide(hemisuccinate)) in 40 μl of 1,4 dioxane and the reaction left stir for 2.5 hr at 4° C. The reaction mixture was then dialyzed for 24 hr at 4° C. in 1500 ml of 0.05 M phosphate buffer to give the title compound which could be used without further purification.

Example 6

Rapamycin 31,42 Diester with Glutaric Acid

The title compound was prepared according to the method used in Example 1.

Example 7

Rapamycin 31,42-diester with (N-hydroxysuccinimide(hemiglutarate)

To a solution of 15.9 mg of rapamycin 31,42-diester with glutaric acid in 160 μL of dimethyl formamide was added 3.65 mg of N,N-dimethylaminopropyl-ethylcarbodiimide and 1.8 mg of N-hydroxysuccinimide. The reaction mixture was allowed to stir until reaction was complete, poured into water, and extracted with ethyl 35 acetate. The organic layers were combined, dried over sodium sulfate, filtered, and concentrated in vacuo to give the title compound, which was stored at 4° C. at 0.1 N sodium phosphate buffer and used without further purification.

Example 8

Rapamycin 31,42-Diester with Glutaric Acid Conjugate with Keyhole Limpet Hemocyanin To 20 mg of keyhole limpet hemocyanin in 2 mL of 0.1 M $NaHCO_3$ was added 55 μL of rapamycin 31,42-diester with (N-hydroxysuccinimide(hemiglutarate)) at 0° C. in 10 μL increments over a 30 min period. The solution was gently shaken until reaction was complete, centrifuged at 6000 rpm for 20 min, and unconjugated starting material was separated from the title compound on a G-25 column with phosphate buffer solution. The conjugate was mixed with glycerol at 50% and stored at −70° C. The number of rapamycin 31,42-diester with glutaric acid moieties per keyhole limpet hemocyanin ranged from 17-45:1

Example 9

Rapamycin 31,42-Diester with Glutaric Acid Conjugate with Ovalbumin

To 20 mg of ovalbumin in 2 mL of 0.1 M $NaHCO_3$ was added 55 μL of rapamycin 31,42-diester with (N-hydroxysuccinimide(hemiglutarate)) at 0° C. in 10 μL increments over a 30 min period. The solution was gently shaken until reaction was complete, centrifuged at 6000 rpm for 20 min, and unconjugated starting material was separated from the title compound on a G-25 column with phosphate buffer solution. The conjugate was mixed with glycerol at 50% and stored at −70° C.

Example 10

Rapamycin 31,42-Diester with Glutaric Acid Conjugate with Horseradish Peroxidase To 10 mg of horseradish peroxidase in 1 mL of 0.1 M NaHCO$_3$ was added 105 μL of rapamycin 31,42-diester with (N-hydroxysuccinimide(hemiglutarate)) in 10 μL increments over a 30 min period. The solution was gently shaken until complete, centrifuged at 6000 rpm for 20 min, and eluted from a G-25 column with phosphate buffer solution. The conjugate was mixed with glycerol at 50% and stored at −20° C.

Example 11

Rapamycin 42-ester with
N-[9H-fluoren-9-ylmethoxy)carbonyl]glycine

To a chilled (0° C.) solution of rapamycin (0.73 g, 0.08 mmol) in methylene chloride (5 mL) was added 0.6 g (1.19 mmol) of N-[(9H-fluoren-9-ylmethoxy)carbonyl]glycine pentafluorophenyl ester, followed by pyridine (0.85 mL, 10.5 mmol) and dimethylaminopyridine (18 mg, 0.14 mmol) to form a heterogeneous solution, which became homogeneous upon warming to room temperature. The reaction mixture was stirred at room temperature overnight. A large excess of EtOAc was added. The organic layer was washed with 0.5 N HCl (2×) and brine, dried (MgSO$_4$), and concentrated to yield an off-white foam. Flash chromatography (30-50% hexane/EtOAc) yielded the title compound in 71% yield (0.679 g, 0.57 mmol). Mass spec (negative ion FAB) M$^-$ at m/z 1192.

Example 12

Rapamycin 42-ester with 3-[3-(4-iminobutylthio) succinimidyl]phenacyl-glycine conjugate with horseradish peroxidase To a solution of rapamycin 42-ester with N-[9H-fluoren-9-ylmethoxy)carbonyl]glycine (10 mg, 8.4 μmol) in acetonitrile (84 μL) was added 10 μL (in acetonitrile at 0.84 M) of diethylamine. The reaction mixture was stirred at room temperature for 60 minutes and the solvent was removed with a stream of nitrogen. The residue was dissolved in acetonitrile (100 μL) and washed with hexane (5 times, 200 μL), followed by concentration of the solvent with a nitrogen stream. The resulting rapamycin 42-ester with glycine was taken up in a solution of m-maleimidobenzoyl-N-hydroxysuccinimide (MBS) (2 mg) in DMF (200 μL) and allowed to incubate for two hours at 4° C., followed by the addition of 50 nM ethanolamine (20 μL) in 50 mM Tris HCl, pH 8.0. Horseradish peroxidase (5 mg) and Rabbit IgG (10 mg) were treated with 2-iminothiolane and purified with Sephadex G-25, followed by the addition of the MBS-rapamycin glycine ester adduct. The mixture was incubated overnight at 4° C. and purified by gel filtration on Sephadex G-25 to provide the title compound.

Example 13

Rapamycin 42 ester with
(N-(3-carboxyphenyl)-3-thiosuccinimidyl)-glycine
conjugate with horseradish peroxidase To a solution of rapamycin 42-ester with N-[9H-fluoren-9-ylmethoxy)carbonyl]glycine (10 mg, 8.4 μmol) in acetonitrile (84 μL) was added 10 μL (in acetonitrile at 0.84 M) of diethylamine. The reaction mixture was stirred at room temperature for 60 minutes and the solvent was removed with a stream of nitrogen. The residue was dissolved in acetonitrile (100 μL) and washed with hexane (5 times, 200 μL), followed by concentration of the solvent with a nitrogen stream. The resulting rapamycin 42-ester with glycine was taken up in a solution of N-succinimidyl S-acetylthioacetate (2 mg) in DMF (200 μL). The reaction mixture was stirred at room temperature for 15 minutes and then at 4° C. overnight. A solution of hydroxylamine HCl (7 mg in 50 μL DMF) was added to the solution of rapamycin reaction mixture, incubated for one hour, followed by the addition of MBS-horseradish peroxidase adduct and MBS-Rabbit IgG to give the title compound which was purified by Sephadex G-25 gel filtration.

Example 14

Rapamycin 1,3, Diels Alder Adduct with Diethyl Azidodicarboxylate

Rapamycin (1 g, 1.093 mmol) and diethyl azodicarboxylate (0.381 g, 2.187 mmol) were dissolved in dichloromethane (10 ml) and heated at 65° C. overnight, TLC showed that the reaction was complete. The mixture was purified on a silica gel column using ethyl acetate as eluant to provide a white solid (0.750 g) which was triturated with hexane and air dried to give the title compound (0.666 g) as a powder.

Anal Calc for $C_{57}H_{89}N_3O_{17}$: C, 62.91; H, 8.24; N, 3.86. Found: C, 62.81; H, 8.12; N, 3.91.

IR (KBr, cm$^{-1}$) 3450, 1720

NMR (CDCl$_3$) δ 6.15 (m, 1H), 5.20 (d, 1H), 3.40 (s, 3H), 3.30 (s, 3H), 3.15 (s, 3H), 0.9 (t, 3H), 0.72 (q, 1H)

MS (−FAB) 1087 (M$^-$)

Example 15

Rapamycin 1,3, Diels Alder Adduct with Phenyltriazolinedione

Rapamycin (0.66 g, 721 mmol) was dissolved in dichloromethane (10 ml) and cooled to 0° C. To this was added, dropwise, a solution of phenyltriazolinedione (0.133 g, 758 mmol) in dichloromethane (10 ml). The solution was stirred overnight, TLC showed the reaction was not complete. Additional phenyltriazenedione (0.025 g, 27 mmol) was added. The reaction was purified using HPLC (4.1×31 cm, SiO$_2$) with ethyl acetate as eluant to provide the title compound as a solid. The solid was triturated with 30 ml of hexane and 1 ml of ethyl acetate filtered and air dried to give the title compound as a powder (0.383 g).

Anal Calc for $C_{59}H_{84}N_4O_{15}$: C, 65.05; H, 7.77; N, 5.14. Found: C, 65.39; H, 7.98; N, 4.92.

IR (KBr, cm$^{-1}$) 3450, 1715

NMR (DMSO) δ 7.50 (m, 3H), 7.40 (m, 2H), 3.11 (s, 3H), 3.00 (s, 3H) 2.95 (s, 3H), 0.8 (q, 1H)

MS (−FAB) 1.088 (M$^-$)

The following are representative examples of fluorescent rapamycin derivatives that can be conjugated via a linker at the 31-position of rapamycin.

Example 16

42-Dansylrapamycin

Rapamycin (200 mg, 0.22 mmol) in dry pyridine (2 ml) was cooled to 0° C. and was treated with dansyl chloride (840 mg, 3.1 mmol). The reaction was warmed to room temperature and stirred for 24 hours. The reaction mixture was poured into cold 2N HCl (30 ml) and was extracted with ethyl acetate (4×25 ml). The ethyl acetate was pooled and washed with brine, dried over $MgSO_4$, filtered and concentrated in vacuo. The residue was chromatographed on silica with 25% ethyl acetate in benzene. This afforded 150 mg of the title compound as a yellow powder, mp 101-104° C.

Example 17

Rapamycin 42-Ester with Pyrene Butyric Acid

Rapamycin (459 mg, 0.5 mmol) and pyrenebutyric acid (216 mg, 0.75 mmol) were dissolved in $THF/CH_2Cl_2$ (10 ml, 1:1). 1-(3-Dimethylaminopropyl)-3-ethyl carbodiimide hydrochloride (146 mg, 0.67 mmol) and 4-dimethylaminopyridine (15 mg) were added to the solution. The reaction was allowed to warm to room temperature over 15 hours. The reaction was diluted with $CH_2Cl_2$ and washed with 5% HCl, then brine. The solution was dried over $MgSO_4$, filtered and evaporated to a solid. The solid was applied to a 3 mm silica gel Chromatron plate which was eluted with 50% ethyl acetate in hexane to provide 180 mg of the title compound as a foam. The reaction also afforded 100 mg of 31,42-diesterified rapamycin.

IR (KBr, $cm^{-1}$) 3420, 1740
NMR ($CDCl_3$) d 8.3 (d, 1H), 8.14 (dd, 2H), 8.10 (d, 2H), 7.85 (d, 1H), 3.34 (s, 3H), 3.30 (s, 3H), 3.11 (s, 3H)
MS (−FAB) 1183 (M−)

The following are representative examples of rapamycin derivatives that can be conjugated to immunogenic carriers by the procedures described above or can be connected to another linker and then conjugated.

Example 18

Rapamycin 42-Carbomethoxymethyl Ether and Rapamycin 42-bis(carbomethoxymethyl ether)

Rapamycin (2.0 g, 2.187 mmol) and rhodium (II) acetate (0.37 g, 0.08 mmol) were heated to reflux in benzene and treated with a solution ethyl diazoacetate (500 ml) in benzene (10 ml) over 10 minutes. The solution was cooled to room temperature and was stirred overnight. TLC showed that the reaction was incomplete. Two additional portions of ethyldiazoacetate (3 ml) were added at 24 hour intervals. The mixture was concentrated and purified by flash chromatography over silica using ethyl acetate. This provided the 42-monoether (1 g) and the 31,42 diether (0.850 g) as oils. The 42-monoether was triturated in a mixture of hexane, ethyl acetate and dichloromethane over the weekend to give the product as a powder. The diether was purified on HPLC on a silica gel column with ethyl acetate as eluant. This provided the product as a solid.
Analytical Data for the Monoether:
Analysis Calc for $C_{55}H_{85}NO_{15}$: C, 66.04; H, 8.57; N, 1.40. Found: C, 65.29; H, 8.64; N, 1.60.

IR (KBr, $cm^{-1}$) 3420, 1715
NMR ($CDCl_3$) d 4.82 (s, 1H), 3.41 (s, 3H), 3.33 (s, 3H), 3.13 (s, 3H), 1.28 (t, 3H), 0.70 (q, 1H)
MS (−FAB) 999 (M−)
Analytical Data for the Diether:
Analysis −Calc for $C_{59}H_{91}NO_{17}$: C, 65.23; H, 8.44; N, 1.29. Found: C, 63.29; H, 8.40; N, 1.44.
IR (KBr, $cm^{-1}$) 1740
NMR ($CDCl_3$) S 6.36 (q, 2H), 5.24 (s, 1H), 3.39 (s, 3H), 3.32 (s, 3H), 3.12 (s, 3H), 0.65 (q, 1H)
MS (−FAB) 1085 (M−)

Example 19

Rapamycin 42-(4-nitrophenyl)carbonate and Rapamycin 31,42-bis(4-nitrophenyl)carbonate Rapamycin (0.450 g, 0.49 mmol) was dissolved in dry dichloromethane (10 ml) and cooled to 0° C. To this solution was added pyridine (0.4 ml, 5.7 mmol) and a crystal of 4-dimethyl aminopyridine. A solution of 4-nitrophenyl chloroformate (0.3 g 1.49 mmol) in dichloromethane (3 ml) was added. The solution was allowed to warm to room temperature overnight and was stirred at room temperature for 24 hours. The reaction was quenched into 0.1N HCl (5 ml) and the aqueous layer was washed with dichloromethane. The organic layer was dried over $MgSO_4$, filtered, and evaporated in vacuo to afford a yellow solid. Chromatography over silica gel with 75% Ethyl acetate in hexane afforded 180 mg of the 42-monocarbonate and 47 mg of the 31,42-dicarbonate as yellow solids.

Example 20

42-O-(Phenoxythiocarbonyl)-rapamycin

Rapamycin (1.030 g, 1.12 mmol) was dissolved in dry dichloromethane (100 ml) and was cooled to 0° C. To this solution was added pyridine (0.27 ml, 3.33 mmol) and a crystal of 4-dimethyl aminopyridine. A solution of thiophenyl chloroformate (0.47 ml 1.49 mmol) in dichloromethane (5 ml) was added to the reaction mixture. The solution was allowed to warm to room temperature overnight and was stirred at room temperature for 24 hours. The reaction was quenched into 0.1N HCl (5 ml) and the aqueous layer was washed with dichloromethane. The organic layer was dried over $MgSO_4$, filtered and evaporated in vacuo to afford a yellow solid. Chromatography on a 4 mm silica gel Chromatotron plate with a gradient of 40% to 70% ethyl acetate in hexane afforded 520 mg of the title compound as a yellow foam.
Analysis Calc for $C_{58}H_{83}NOS_{14}$: C, 66.32; H, 7.97; N, 1.33. Found: C, 66.48; H, 8.05; N, 1.12.
IR (KBr, $cm^{-1}$) 3420, 1715
NMR ($CDCl_3$) δ 7.41 (t, 1H), 7.25 (t, 2H), 7.12 (d, 1H), 3.45 (s, 3H), 3.33 (s, 3H), 3.13 (s, 3H)
MS (−FAB) 1049 (M−)

Example 21

Rapamycin-O-carboxymethyl-27-oxime

To a solution of 600 mg (650 μM) of rapamycin in 6 mL of methanol was added at room temperature, 100 mg (1.2 mmol) of anhydrous sodium acetate and 140 mg (660 μM) of carboxymethoxylamine hemihydrochloride. After stirring overnight at room temperature, the reaction was complete. The reaction mixture was concentrated in vacuo and the residue was triturated with water. The solids were filtered and washed thoroughly with water. The product was dried under high vacuum to give 575 mg (89.7%) of a white solid. $^{13}$C and $^{1}$H NMR indicated a mixture of E and Z isomers for the oxime derivative at position 27.

$^{1}$H NMR (CDCl$_3$, 400 MHz): 3.43 and 3.41 (2s, 3H, CH$_3$O), 3.30 (s, 3H, CH$_3$O), 3.18 and 3.12 (2s, 3H, CH$_3$O), 1.82 (s, 3H, CH$_3$C=C), 1.695 and 1.633 (2s, 3H, CH$_3$C=C); $^{13}$C NMR (CDCl$_3$, MHz): 215.8 (C=O), 211.5 (C=O), 194.5 (C=O), 191.0 (C=O), 172.5 (C=O), 169.0 (C=O), 168.5 (C=O), 167.0 (C=O), 161.5 (C=NOC), 160.0 (C=NOC), 140.0; MS (neg. ion FAB: 985 (M−H)$^-$, 590, 167, 128, 97, 75 (100%)

Analysis Calcd for C$_{53}$H$_{82}$N$_2$O$_{15}$ 0.15H$_2$O: C, 63.90; H, 8.40; N, 2.81.

Found: C, 63.81; H, 8.41; N, 2.85.

The following compound was used in the generation of rapamycin specific antibodies.

Example 22

Rapamycin 42-Ester with Glycylbiotin

To a solution of biotin (0.83 g, 3.4 mmol) in 60 mL of DMF was added glycine t-butyl ester hydrochloride (0.57 g, 3.4 mmol), N methylmorpholine (0.92 mL, 8.36 mmol), 1-hydroxybenzotriazole (0.61 g, 3.99 mmol) and 1-(3-Dimethylaminopropyl)-3-ethylcarbodiimide hydrochloride (0.65 g, 3.4 mmol). The reaction mixture was stirred at room temperature for 7 days. The DMF was concentrated, ethyl acetate was added, and the organic layer was washed with water, 0.5 N HCl, saturated sodium. bicarbonate, and brine. The ethyl acetate layer was dried (MgSO$_4$) and concentrated to yield tert-butylglycylbiotin as a white solid which was primarily one spot on TLC (0.611 g, 1.71 mmol, 50/o). Mass spec [M+H]$^+$ at m/z 358.

To a solution of tert butylglycylbiotin (0.271 g, 0.758 mmol) in CH$_2$Cl$_2$ (0.5 mL) was added 0.5 mL trifluoroacetic acid. The reaction mixture was stirred at room temperature for 2 h, concentrated, and triturated with anhydrous diethyl ether. The off-white precipitate was collected to yield 0.209 g (0.694 mmol, 92%) of glycylbiotin. Mass spec [M+H]$^+$ at m/z 302.

To a solution of glycylbiotin (0.65 g, 2.16 mmol) in 1-methylpyrrolidinone (5 mL) was added 6 mL of CH$_2$Cl$_2$, causing a precipitate to form which persisted even after the addition of 0.33 mL (2.36 mmol) of triethylamine. To this heterogenous solution was added 2 g (2.19 mmol) of rapamycin, 0.43 g (2.24 mmol) of 1-(3-dimethylaminopropyl)-3-ethylcarbodiimide hydrochloride, and 30 mg (2.46 mmol) of DMAP. After several hours, the reaction mixture became homogenous, and was stirred an additional four days. A large excess of ethyl acetate was added and the organic layer was washed with water, 0.5 N HCl, saturated sodium bicarbonate, and brine. The organic layer was dried (MgSO$_4$) and concentrated. The light yellow foam was triturated with hot anhydrous diethyl ether to yield 1.2 g of impure title compound as a light yellow solid. A portion (0.5 g) of this material was flash chromatographed in 5% MeOH/CHCl$_3$, and triturated again in hot ether to yield 87 mg of the title compound contaminated with a small amount of rapamycin. This material was rechromatographed (gradient 0-5% MeOH/CHCl$_3$), and triturated a final time with ether to yield 34 mg (0.028 mmol) of pure title compound as a white solid. Mass spec, negative FAB M$^-$ at m/z 1196.

What is claimed is:

1. A monoclonal antibody which specifically recognizes a rapamycin, obtained or obtainable by:
    a) reaction of a rapamycin having an activate coupling group at least one of positions 42 or 31 with an immunogenic protein to produce an immunogenic conjugate,
    b) administration of said immunogenic conjugate to an appropriate animal species to effect immunogenic challenge and recovery of antibody-producing cells sensitized to said conjugate,
    c) immortalization of said antibody-producing cells, and
    d) recovery of monoclonal antibody from a selected immortalized cell line thus established.

2. An immunogenic conjugate comprising a rapamycin conjugated at least one of positions 27, 42 or 31 to an immunogenic carrier protein.

3. An immunogenic conjugate according to claim 2 which is produced by reacting an immunogenic carrier protein with a rapamycin derivative bearing an activated coupling group at least one of positions 27, 42 or 31.

4. A rapamycin having an activated coupling group at least one of positions 27, 42 or 31.

5. A hybridoma cell line capable of producing a monoclonal antibody as defined in claim 1.

6. An immunoassay kit for measuring the blood level of a rapamycin, comprising a monoclonal antibody as defined in claim 1.

7. The immunogenic conjugate according to claim 2, which is produced by reacting an immunogenic protein with a rapamycin bearing an activated coupling group at least one of positions 27, 42 or 31.

* * * * *

UNITED STATES PATENT AND TRADEMARK OFFICE
CERTIFICATE OF CORRECTION

| | | |
|---|---|---|
| PATENT NO. | : 7,897,733 B2 | |
| APPLICATION NO. | : 11/272070 | |
| DATED | : March 1, 2011 | |
| INVENTOR(S) | : Katherine L. Molnar-Kimber et al. | |

It is certified that error appears in the above-identified patent and that said Letters Patent is hereby corrected as shown below:

Title Page
Column 1, Item (73) the Assignee should be "Wyeth" – not "Pfizer, Inc."

Signed and Sealed this
Twelfth Day of July, 2011

David J. Kappos
*Director of the United States Patent and Trademark Office*